(12) United States Patent
Dave et al.

(10) Patent No.: US 8,058,391 B2
(45) Date of Patent: Nov. 15, 2011

(54) PROCESS FOR THE PREPARATION OF INSULIN CONJUGATE IN-105

(75) Inventors: Nitesh Dave, Bangalore (IN); Partha Hazra, Bangalore (IN); Anuj Goel, Bangalore (IN); Nita Roy, Bangalore (IN); Anand Khedkar, Bangalore (IN); Harish Iyer, Bangalore (IN); Gautam Krishnan, Bangalore (IN); H. S. Manjunath, Bangalore (IN); Shrikumar Suryanarayan, Bangalore (IN); Govindasamy Manikam, Bangalore (IN); Goldy Sachdev, Bangalore (IN); Mayank Garg, Bangalore (IN)

(73) Assignee: Biocon Limited (IN)

( * ) Notice: Subject to any disclaimer, the term of this patent is extended or adjusted under 35 U.S.C. 154(b) by 871 days.

(21) Appl. No.: 12/083,275

(22) PCT Filed: Oct. 13, 2005

(86) PCT No.: PCT/IN2005/000338
§ 371 (c)(1),
(2), (4) Date: Apr. 7, 2008

(87) PCT Pub. No.: WO2007/043059
PCT Pub. Date: Apr. 19, 2007

(65) Prior Publication Data
US 2011/0020871 A1    Jan. 27, 2011

(51) Int. Cl.
*C07K 14/62* (2006.01)
*C07K 1/14* (2006.01)
*C07K 1/10* (2006.01)
*C07K 1/06* (2006.01)
*A61K 38/28* (2006.01)

(52) U.S. Cl. ........ 530/305; 530/303; 530/304; 530/402; 530/412; 530/416; 424/124; 514/6.3; 514/6.4

(58) Field of Classification Search ................. None
See application file for complete search history.

(56) References Cited

U.S. PATENT DOCUMENTS

| | | |
|---|---|---|
| 4,179,337 A | 12/1979 | Davis |
| 4,338,306 A | 7/1982 | Kitao |
| 4,579,730 A | 4/1986 | Kidron |
| 5,283,236 A | 2/1994 | Chiou |
| 5,359,030 A | 10/1994 | Ekwuribe |
| 5,567,422 A | 10/1996 | Greenwald |
| 5,658,878 A | 8/1997 | Backstrom |
| 5,853,748 A | 12/1998 | New |
| 6,011,008 A | 1/2000 | Domb |
| 6,022,524 A | 2/2000 | Maisano |
| 6,200,602 B1 | 3/2001 | Watts |
| 6,309,633 B1 | 10/2001 | Ekwuribe |
| 6,828,297 B2 | 12/2004 | Ekwuribe |

FOREIGN PATENT DOCUMENTS

| | | |
|---|---|---|
| WO | WO 02/098232 | 12/2002 |
| WO | WO 03/022208 | 3/2003 |
| WO | WO 03/022996 | 3/2003 |
| WO | WO 2004/083234 | 9/2004 |
| WO | WO 2005/016312 | 2/2005 |

OTHER PUBLICATIONS

Internatioanl Preliminary Report on Patentability Feb. 1, 2008.
International Search Report Mar. 8, 2006.
International Written Opinion Aug. 31, 2006.
Still JG, "Development of oral insulin: progress and current status," *Diabete Metab Res Rev* 18:S29-S37 (2002).

*Primary Examiner* — Elly-Gerald Stoica
(74) *Attorney, Agent, or Firm* — Ballard Spahr LLP

(57) ABSTRACT

The invention claims a process for making an insulin-oligomer conjugate IN-105. IN-105 precursor having formula G-A-V-R-[B-Chain]-R-D-A-D-D-R-[A-Chain] is cloned and expressed in *Pichia*. The biosynthetic precursor is then conjugated with an activated oligomer. The IN-105 precursor-oligomer conjugate is then treated with protease and purified to afford active insulin-oligomer conjugate of formula insulin-OC—$CH_2$—$CH_2$—$(OCH_2CH_2)_3$—$OCH_3$.

15 Claims, No Drawings

SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 1

Gly Ala Val Arg Arg Asp Ala Asp Asp Arg
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 2

Gly Ala Val Arg
1

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 3

Ala Ala Arg Ala Ala Arg Gly Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 4

His His His His His His Ala Ala Arg
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 5

His His Ala His Ala His Ala His Ala Ala Arg
1               5                   10

<210> SEQ ID NO 6
<211> LENGTH: 6
<212> TYPE: PRT
<213> ORGANISM: Artificial Sequence
<220> FEATURE:

```
<223> OTHER INFORMATION: Description of Artificial Sequence: Note =
      Synthetic Construct

<400> SEQUENCE: 6

Arg Asp Ala Asp Asp Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 7

Arg Asp Ala Leu Gln Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 8

Arg Glu Glu Ala Glu Ala Glu Ala Glu Pro Arg
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 9

Arg Pro Gly Arg
1

<210> SEQ ID NO 10
<211> LENGTH: 117
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
ggtgctgtta gagttaacca acatttgtgt ggttctcatt tggttgaagc tttgtacttg      60
gtttgtggtg aaagaggttt tttttacact ccaaagacta gagatgctga tgataga       117

<210> SEQ ID NO 11
<211> LENGTH: 61
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 11

Gly Ala Val Arg Phe Val Asn Gln His Leu Cys Gly Ser His Leu Val
1               5                   10                  15

Glu Ala Leu Tyr Leu Val Cys Gly Glu Arg Gly Phe Phe Tyr Thr Pro
```

```
                    20                  25                  30
Lys Thr Arg Asp Ala Asp Asp Arg Gly Ile Val Glu Gln Cys Cys Thr
            35                  40                  45

Ser Ile Cys Ser Leu Tyr Gln Leu Glu Asn Tyr Cys Asn
        50                  55                  60
```

PROCESS FOR THE PREPARATION OF INSULIN CONJUGATE IN-105

CROSS REFERENCE TO RELATED APPLICATIONS

The present application is a National Phase Application of International Application No. PCT/IN2005/000338 filed Oct. 13, 2005, which application is incorporated herein fully by this reference.

FIELD OF THE INVENTION

The present invention relates to a process for an insulin-oligomer conjugate of formula insulin-oligomer. The process involves cloning and expression of an precursor IP-F of formula G-A-V-R-[B-Chain]-R-D-A-D-D-R-[A-Chain] and subjecting the expressed biosynthetic precursor to conjugation with an activated oligomer followed by protease treatment and purification to get an active insulin-oligomer conjugate.

BACKGROUND OF THE INVENTION

The β-cells of the pancreatic islets secrete a single chain precursor of insulin, known as pro-insulin which upon proteolysis results in the biologically active polypeptide insulin. The insulin molecule is a highly conserved across species and generally consists of two chains of amino acids linked by disulfide bonds. The natural human insulin molecule (mw 5,807 Daltons), has A-chain of 21 amino acid residues with glycine at the amino terminus; and a B-chain of 30 amino acid residues with phenylalanine at the amino terminus. Insulin may exist as a monomer or may aggregate into a dimer or a hexamer formed from three of the dimers. The monomer has the ability to bind to receptors and is the biologically active form.

Insulin polypeptide is the primary hormone responsible for controlling the transport, utilization and storage of glucose in the body. A defect in the carbohydrate metabolism as a result of insufficient production of insulin or reduced sensitivity of the receptor to insulin leads to the biological disorder diabetes. Diabetes impairs the normal ability to use glucose as a result increases blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness. Diabetes when left untreated leads to ketosis, followed by acidosis with nausea and vomiting. As the toxic products continue to build up, the patient goes into a diabetic coma, which leads to the patient's death. There are two types of diabetes Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases insulin is required.

Traditionally bovine and porcine insulin were used almost exclusively to treat diabetes in humans. With the development of recombinant technology commercial scale manufacture of human insulin was made possible by fermentation. Furthermore, genetically engineered insulin analogs having biological activity comparable to that of natural human insulin were developed to combat the disease. However, treatment of diabetes typically requires regular injections of insulin. Due to the inconvenience of insulin injections, various approaches have been attempted to formulate insulin for administration by non-injectable routes. A list of such publications include: U.S. Pat. No. 4,338,306 (Kitao et al.) reports a pharmaceutical compositions of insulin and fatty acids having 8 to 14 carbon atoms and nontoxic salts thereof for rectal administration of insulin; U.S. Pat. No. 4,579,730 (Kidron et al) reports an enterocoated insulin compositions with a bile acid or alkali metal salt thereof for the oral administration of insulin; U.S. Pat. No. 5,283,236 (Chiou et al.) reports an insulin composition with a permeation-enhancing agent to aid systemic absorption of higher molecular weight polypeptides, as well as peptidase inhibitors for systemic delivery of insulin through the eyes wherein the drug passes into the nasolacrimal duct and becomes absorbed into circulation; U.S. Pat. No. 5,658,878 (Backstrom et al.) reports an insulin and sodium salt of a saturated fatty acid of carbon chain length 10 (i.e., sodium caprate), 12 (sodium laurate), or 14 (sodium myristate) which enhances the absorption of insulin in the lower respiratory tract; U.S. Pat. No. 5,853,748 (New et al.)—reports an enteric-coated composition of insulin, a bile salt or bile acid, and carbonate or bicarbonate ions, used to adjust the pH of the gut to a pH of from 7.5 to 9 for the oral administration of insulin. U.S. Pat. No. 6,200,602 (Watts et al) reports a drug delivery composition of insulin for colonic delivery of insulin with an absorption promoter which includes a mixture of fatty acids having 6 to 16 carbon atoms and its salts or a mixture of mono/diglycerides of medium chain fatty acids along with a dispersing agent, in a coating to prevent the release of the insulin and absorption promoter until the tablet, capsule or pellet reaches the proximal colon.

Several attempts to deliver insulin by oral administration are found in literature. The problems associated with oral administration of insulin to achieve euglycemia in diabetic patients are well documented in pharmaceutical and medical literature. Digestive enzymes in the GI tract rapidly degrade insulin, resulting in biologically breakdown products. In the stomach, for example, orally administered insulin undergoes enzymatic proteolysis and acidic degradation. Survival in the intestine is hindered by excessive proteolysis. In the lumen, insulin is barraged by a variety of enzymes including gastric and pancreatic enzymes, exo- and endopeptidases, and brush border peptidases. Even if insulin survives this enzymatic attack, the biological barriers that must be traversed before insulin can reach its receptors in vivo may limit oral administration of insulin. For example, insulin may possess low membrane permeability, limiting its ability to pass from the lumen into the bloodstream.

Pharmaceutically active polypeptides such as insulin have been conjugated with polydispersed mixtures of polyethylene glycol or polydispersed mixtures of polyethylene glycol containing polymers to provide polydispersed mixtures of drug-oligomer conjugates; U.S. Pat. No. 4,179,337 (Davis et al) reports conjugating polypeptides such as insulin with various polyethylene glycols such as MPEG-1900 and MPEG-5000 supplied by Union Carbide. U.S. Pat. No. 5,567,422 (Greenwald) reports the conjugation of biologically active nucleophiles with polyethylene glycols such as m-PEG-OH (Union Carbide), which has a number average molecular weight of 5,000 Daltons.

Conjugation of polypeptides such as insulin with polyethylene glycol modified glycolipid polymers and polyethylene glycol modified fatty acid polymers are reported in U.S. Pat. No. 5,359,030 (Ekwuribe et al.).

U.S. Pat. No. 6,011,008 (Domb et al.) reports a method for producing a water-soluble polysaccharide conjugate of an oxidation-sensitive substance comprising activating the polysaccharide to a dialdehyde by periodate oxidation; (b)

purifying the dialdehyde from interfering anions and by-products; and (c) coupling the substance to the purified dialdehyde by Schiff base formation to form the conjugate. Optionally, the conjugate of step (c) is reduced to an amine conjugate by a reducing substance. Insulin was conjugated to oxidized AG (arabinogalactan) via an amine or imine bond by reacting a solution of pure oxidized AG (arabinogalactan) in borate buffer solution at pH 8.9 with insulin at 4° C. overnight. The clear solution was dialyzed through a cellulose dialysis and the solution was lyophilized to yield 115 mg of a white solid.

U.S. Pat. No. 6,022,524 (Maisano et al.) reported conjugation of Gd-DTPA with porcine insulin in a solution of DTPA and dimethylsulfoxide (DMSO) which was prepared by heating and stirring, then cooled at room temperature and added with a solution of 11.73 g NHS (0.102 mol) in 300 ml DMSO, then, drop by drop, with a solution of 19.6 g of N,N'-dicyclohexylcarbodiimide (0.097 mol) in 400 ml DMSO. The mixture is stirred for 16 hours, then filtered and the filtrate is concentrated by evaporation at 50.degree. C. and 5 Pa to a thick oil of an about 160 ml volume.

U.S. Pat. No. 6,309,633 (Ekwuribe et al.)—reports the use of solid insulin for conjugation of insulin with laurate $PEG_5$ in presence of Triethylamine and DMSO at room temperature. The reaction was monitored via HPLC every 30 mins. The conjugate was purified using a preparative HPLC.

U.S. Pat. No. 6,828,297 (Ekwuribe et al.) reports methods for making PEG7-Hexyl-Insulin by using zinc or zinc free human insulin for conjugation with activated oligomer and purification of B29 modified PEG7-Hexyl-Insulin, insulin in dimethylsulfoxide and triethyl amine was reacted with activated oligomer at 22+/−4° C. The crude reaction mixture is dialyzed or difiltered to remove organic solvents and small molecular weight impurities, exchanged against ammonium acetate buffer and lyophilized; which is further subjected to RP-HPLC equilibrated with 0.5% triethylamine/0.5% phosphoric acid buffer (TEAP A). The column was eluted with a gradient flow using TEAP A and TEAP B (80% acetonitrile and 20% TEAP A) solvent system. Fractions containing the conjugate were pooled and the elution buffer and solvent were removed by dialysis or diafiltration against ammonium acetate buffer and lyophilized to produce white powder of PEG7-hexyl-insulin, B29 monoconjugate (purity>97%). Currently, the existing prior art teaches use of pure insulin powder or crystals as the starting material for making conjugated insulin wherein the insulin used is a biologically active form.

The instant invention facilitates the making of insulin-oligomer conjugate from the precursor IP-X of formula Z-[B-Chain]-Q-[A-Chain], where Z is a leader where Z is a leader peptide sequence, B-Chain is B chain of human insulin or its analog, Q is a linker peptide sequence between the A and B chain, A-chain is the A chain of human insulin or its analog.

The precursor IP-X is conjugated with an oligomer at the $LysB^{29}$ position on the B-chain and the N-terminus amino acid of the leader peptide Z. The IP-X-oligomer conjugate is then subjected to protease treatment followed by purification to get an active insulin-oligomer conjugate.

The starting material is the fermented broth containing the precursor IP-X. The broth containing the IP-X is subjected to a combination of chromatography like ion-exchange, HPLC, RP-HPLC and crystallization to purify the IP-X.

The instant invention is a more simplified and economical in the making of an insulin-oligomer conjugate wherein several steps involved in obtaining pure insulin crystals in biologically active form are circumvented e.g, transpeptidation of the insulin precursor and cleaving the insulin precursor to get the active insulin and several chromatographic purification steps e.g., ion-exchange chromatography, HPLC and RP-HPLC to get the pure insulin crystals.

SUMMARY OF THE INVENTION

The instant invention relates to the process of manufacturing insulin-oligomer conjugate IN-105 comprising, expressing the IN-105 precursor IP-F of formula G-A-V-R-[B-Chain]R-D-A-D-D-R-[A-Chain], treating IP-F with an activated oligomer which conjugates at the $LysB^{29}$ position of the IP-F and at the N-terminus amino acid $Gly^1$ of the leader peptide GAVR. The IP-F is subjected to conjugation with an oligomer having the general formula —OC—$(CH_2)_n$—$(OCH_2CH_2)_n$—$OCH_3$ where n is an integer 1 to 8 and where both the n are different or the same; in the preferred embodiment the activated oligomer has a molecular formula $C_{14}H_{23}NO_8$ (CAS. no. 622405-78-1), to obtain IN-105 of formula insulin-OC—$CH_2$—$CH_2$—$(OCH_2CH_2)_3$—$OCH_3$.

The instant invention involves the use of biosynthetic precursor sequence IP-F of formula G-A-V-R-[B-Chain]-R-D-A-D-D-R-[A-Chain]. The leader sequence G-A-V-R used in the present invention does not have any negatively charged amino acids as required for enhanced expression of insulin in yeast as disclosed in the literature. The process of the instant invention is a more simplified and economical in the making of an insulin conjugate wherein several steps of purification to obtain pure insulin in biologically active form are circumvented. The instant invention results in a product with no conjugation on the A chain or C-peptide (RDADDR) of IN-105 precursor IP-F and wherein the conjugation takes place on the B chain ($LysB^{29}$), and at Gly of the leader chain G-A-V-R which is then subjected to protease treatment to get insulin-oligomer conjugate IN-105. The overall cost of production of the conjugated insulin as a result of this process is minimized.

DETAILED DESCRIPTION

IP-X represents a insulin-oligomer precursor of formula Z-[B-Chain]-Q-[A-Chain], where Z is a leader peptide sequence, B-Chain is B chain of human insulin or its analog, Q is a linker peptide sequence between the A and B chain, A-chain is the A chain of human insulin or its analog. Leader peptides include for example the peptides, GAVR, ARR, AARAARGR, HHHHHHAAR, and HHAHAHAHAAR. The linker peptide Q include, for example, RDADDR, RDALQR, REEAEAEAEPR, RPGR, RAR, RR, and R.

The IP-X precursor may be produced by any suitable expression system such as *Escherichia coli*, *Pichia pastoris*, *Saccharomyces cerevisiae*, CHO cells and the like.

In the instant invention the most preferred embodiment of IP-X, is where the leader sequence Z is GAVR, B-chain is B(1-30) of human insulin, linker peptide Q is RDADDR, and A-chain is A(1-21) of human insulin. The IP-X precursor represented by the formula G-A-V-R-[B-Chain]-R-D-A-D-D-R-[A-Chain] is herein after termed IP-F. The IP-F is of is cloned in-frame with the Mat-alpha signal peptide in the *Pichia pastoris* expression vector, pPIC9K. *Pichia pastoris* host strain, GS115 is transformed with the recombinant plasmid to obtain a *Pichia* clone expressing IPF. The secreted IP-F is treated with trypsin, carboxpeptidase B and N-hydrosuccinamide ester (activated oligomer) to yield IN105.

SEQUENCE FOR THE IN-105 PRECURSOR IP-F.

leader sequence          B-Chain ggtgctgttaga|ttgttaaccaacatttgtgtggttctcatttggttgaagctttgtac

G A V R | V N Q H L C G S H L V E A L Y

B-chain          linker-peptide ttggtttgtggtgaaagaggttttttttacactccaaagactaga|gatgctgatgataga

L V C G E R G F F Y T P K T | R D A D D R

A-Chain ggtattgttgaacaatgttgtacttctatttgttctttgtaccaattggaaaactactgtaac

G I V E Q C C T S I C S L Y Q L E N Y C N

Sequence: Codon optimize for expression in Pichia pastoris

Predicted Molecular weight: 6907.82 Da

Estimated pI value: 5.46 nucleotide (183 bp) and amino acid (61 aa)

The IN-105 precursor IP-F is secreted by *P. pastoris* into the culture medium. The broth is centrifuged and cells are separated from the supernatant. There are multiple options available for the capture of the precursor IP-F including Hydrophobic Interaction chromatography and Ion Exchange chromatography. In the instant invention, cation exchange chromatography and HIC is used to capture the IP-F.

Crystallization of the IN-105 precursor IP-F, removes any impurities carried through from the fermentation broth into the SP-Sepharose elution pool, this helps to reduce column fouling at the RP-HPLC-1 stage. Ammonium acetate salt, which is used to elute the product from the ion exchange column, is also removed by Crystallization. A pure crystalline precursor also helps in reducing cost in the subsequent conjugation step and increases the efficiency of the reaction. The crystalline form can be frozen and stored which would to be substantially stable for multiple days when stored at −20° C.

IN-105 is produced by a reaction wherein IP-F is first conjugated at $B^{29}$ Lysine using an activated oligomer to give IP-F-oligomer conjugate. The IP-F-oligomer conjugate is subjected to protease treatment, where the linker-peptide (RDADDR) and the leader sequence (GAVR) are cleaved to get the an active insulin-oligomer conjugate. The two proteases used are trypsin and carboxypeptidase B. As the $LysB^{29}$ is blocked by the oligomer, the probability of trypsin cleavage at $LysB^{29}$ is minimum. But the other probable sites for trypsin cleavage are c-terminus end of B-22 (Arg), C-1 (Arg) and C-6 (Arg). A $2^{nd}$ protease (carboxypeptidase B) treatment is done to remove the free basic (Arg) amino acid from the B chain, where one extra Arg is attached with the B-30(Thr) to get final product IN-105. The two protease treatment is carried out in a single operation at optimum reaction condition where yield was maximized with minimum product related impurities generated.

After the enzyme cleavage reaction is completed, the impurities may be separated from IN-105 e.g., the first RP-HPLC step. In the instant invention the impurities are removed when the first RP is run at low pH and final purification is done at high pH. A low loading and a gradient starting from 20 to 35 was carried out at 15 g/L of resin loading. The first RP-HPLC step gave a purity of ~93-95%. There were a number of impurities which needed to be removed, where the impurities remaining after the first RP-HPLC step are purified by subjecting the elution pool of to another round of RP-HPLC. The final product of IN-105 had a purity to 97-98%.

Although RP-HPLC is one of most preferred steps for purification of closely related impurities, low-pressure chromatography using different techniques of purification like ion exchange, HIC (Hydrophobic Interaction Chromatography) etc can also be used.

EXAMPLES

Example 1

Expression of IN105 Precursor IP-F in *Pichia pastoris* pPIC9K/IP-F plasmid was digested with Bgl II and used to transform electrocompetent cells of *P. pastoris* GS115 (his4). Regeneration mix was plated onto YNBD agar (1.34% Yeast Nitrogen Base without amino acids, 2% Dextrose, 2% agar) plates and incubated at 30° C. for 48 hours. Colonies were grown in YPD (1% Yeast extract, 2% Peptone, 2% Dextrose) broth in micro titre plates along with appropriate controls. The plates were then stamped onto YPD agar (1% Yeast extract, 2% Peptone, 2% Dextrose, 2% agar) plates containing Geneticin (G418) and incubated at 30° C. for 48 hours. Clones resistant to 1-3 mg/ml G418 were used for expression studies.

Genomic DNA was made from the selected recombinant *Pichia* clones using zymolyase enzyme for lysis. PCR was carried out using gene specific primers to confirm the integration of IP-F in the genome. GS115 host strain was used a negative control.

Expression studies in *P. pastoris* was carried out wherein the clones were grown at 30° C. in BMGY (1% Peptone, 2% Yeast extract, 1.34% Yeast Nitrogen Base, 2% glycerol, $4\times10^{-5}$% Biotin, 100 mM phosphate buffer, pH 6.0). This was followed by induction with methanol in BMMY (1% Peptone, 2% Yeast extract, 1.34% Yeast Nitrogen Base, 0.5% Methanol, $4\times10^{-5}$% Biotin, 100 mM phosphate buffer, pH 6.0). Induction with methanol was carried out for a total of 3 days. The crude supernatant from each of the clones was analysed on SDS-PAGE stained with Coomassie blue. IP-F was secreted as a ~7 kDa protein.

The clones were analysed for secretion of IP-F for three days after methanol induction in shake flasks. An HPLC method was used for the analysis using Symmetry C18 column (4.6×250 mm, 300 $A^{O}$, 5 micron, Waters) and Buffers A (0.1% TFA in water) and B (100% Acetonitrile). The column is equilibrated with 25% Buffer A prior to sample injection. A programmed gradient is applied at a flow rate of 1 ml/min for the sample estimation: a linear gradient of 25% buffer A to 40% buffer A is made in the first 15 minutes of the programmed gradient after the sample injection; 40% Buffer A is maintained for the 15th and 16th minutes of the program; then the concentration of Buffer A is brought back to 25% by using gradient between 16th to 18th minutes; the concentration of Buffer A is kept constant in the run for the last 5 minutes to equilibrate the column for the next run.

Example 2

A loop full of culture from a single isolated colony grown on seed medium (1% Yeast extract, 0.5 peptone, 2% agar and 20% dextrose monohydrate) is cultivated in 250 ml flask containing 50 ml BYYG medium (1% Peptone, 2% Yeast extract, 1.34% Yeast nitrogen base, 2% glycerol and 10% 1M phosphate buffer of pH 6.0) at 30+/−1 deg C. and 230+/−10 rpm. After 48~50 hrs of incubation the optical density measured at 600 nm reaches 10+/−2. The cells were resuspended in to 6 ml of production medium (1% Peptone, 2% Yeast extract, 1.34% Yeast nitrogen base, 0.5% methanol and 10% 1 M phosphate buffer of pH 6.0) in 100 ml flask in order to make 50% w/v cell suspension. Flasks were incubated at 30 deg C. 30 micro L of Methanol was added to all flasks every day from 2nd day. Assay on $4^{th}$ day was 0.069 g/L.

Example 3

The seed flasks were prepared by cultivating frozen (−85° C.) cells of *Pichia* in 250 ml flask containing 50 ml growth medium (1% yeast extract, 2% peptone, 10% 1 M phosphate buffer of pH 6.0, 0.67% Yeast nitrogen base and 0.1% glycerol) at 30+/−1 deg C. and 230+/−10 rpm. After 20-28 hrs of incubation, OD (600 nm) reaches 10-12. These cells were further cultivated in 2 L fermentor containing one liter fermentation medium consisting of 4% glycerol, 0.0093% calcium sulfate, 1.82% potassium sulfate, 1.49% magnesium sulfate, 0.0413% potassium hydroxide. Fermentor was run at 30 deg C. and pH of 5.0. The aeration rate was set to 0.1-1.0 vvm. Agitation speed was adjusted to maintain the dissolved oxygen above 10%. Biomass was build up to 300-400 g/L by 50% glycerol feeding. Methanol was fed for induction. Assay on day 5 of methanol feeding is 0.76 g/L.

Example 4

Selective Conjugation

IN-105 is prepared from the cell free fermentation broth containing the IN-105 precursor by steps comprising of,
a) SP-Sepharose column was equilibrated with buffer A(2C.V), pH of the cell free broth was adjusted to 4.0 with glacial acetic acid and the supernatant was loaded on to column at 45 g/L of resin. Washing was done using Buffer A (1.5 C.V) and product was eluted at 60% of Buffer B. The elution pool was concentrated 8 times and Yield was 95%. [Buffer A-10 mM Ammonium Acetate pH 4.0; Buffer B-1 M Ammonium Acetate pH 4.0].
b) the elution pool containing the IN-105 precursor was taken in 1:1 dilution with water and the pH was adjusted to 5.0 with 10 N NaOH. 0.4% (v/v) of phenol and 4% (v/v) of 0.3 N zinc chloride was added. The mixture kept under cold condition for 6-8 hrs for crystallization. The recovery of IN-105 precursor was 95%.
c) 6 g of the wet pellet containing the IN-105 precursor crystals was taken and 32 ml of 500 mM borate buffer of pH 8.1 was added to it. The pH was adjusted to 10.5 with 10 N NaOH. 370 mg Oligomer dissolved in 11 ml of acetonitrile was added and the contents were stirred. Yield of total conjugated product was around 78%
d) Equal volume of the conjugated product from step (c) and water was taken. The pH of the solution was adjusted to 5.0 with glacial acetic acid then 0.4% (v/v) of phenol and 4% (v/v) of 0.3 N zinc chloride was added was added to the mixture and the pH was adjusted to 5.1 with 1 N NaOH. The mixture was kept over night at 4° C. for crystallization. Yield in this step was 90%,
e) the wet crystal pellet from step (d) was solubilized in 0.5 M tris base solution to make the a product concentration of 16 g/l. The pH of the solution was made 7.4 using 1 N NaOH. Then 0.027 mM of trypsin and $0.3 \times 10^{-3}$ mM of carboxypeptidase B was added to the reaction mixture and kept at 24° C. for 12 hrs. The product formed was IN-105 with a step yield of 80%,
f) A column packed with resin of particle size:10-15 μ, pore size: 120 Å was equilibrated using 15% B, the reaction mixture from step (e) was diluted 1:10 and pH was adjusted to 7.0 before loading, and washing was done with 15% B. Elution was done using 15 to 25% B over 20 Cvs. Fractions of 95% purity were got [Buffer A: 10 mM Sodium Acetate pH 7.0; Buffer B:100% Acetonitrile].
g) The eluent from step (f) is further diluted and pH is adjusted to 8.5 before loading, and washing was done with 20% B. Elution was done using 20 to 35% B over 15 CVs. Fractions of 97% purity were got [Buffer A: 100 mM Tris pH 8.5; 20 mM Magnesium Chloride; Buffer B:Acetonitrile]
h) The elution pool from step (g) was taken and the concentration of IN-105 was brought down to 6 mg/ml by dilution with water. The pH of the sample was adjusted to 4.5 with glacial acetic acid. 0.6% (v/v)phenol and 4% (v/v) of 0.3 N zinc chloride were added and pH was finally made to 5 and the mixture was kept at 4° C. overnight to form crystals. The crystals were collected after centrifugation with a step yield of 90%.

Example 5

Selective Conjugation

IN-105 is prepared from the cell free fermentation broth containing the IN-105 precursor by steps comprising of,
a) Taking the Cell free broth at pH 7 was loaded onto a column packed with PLRP S 50-70 MICRON. The broth was made to 5% MeCN and loaded onto the column, which was equilibrated with 10 mM Sodium acetate pH 7.0 and 5% MeCN. A recovery of 90% from 4 g/L loading was got,
b) the elution pool containing the IN-105 precursor was taken in 1:1 dilution with water and the pH was adjusted to 5.0 with 10 N NaOH. 0.4% (v/v) of phenol and 4% (v/v) of 0.3 N zinc chloride was added. The mixture kept under cold condition for 6-8 hrs for crystallization. The recovery of IN-105 precursor was 95%.
c) 20 g of the wet pellet containing IN-105 precursor crystals was taken and 92 ml of 500 mM borate buffer of pH 8.1 was added. The pH was adjusted to 10.5 using 0.10 N NaOH; 1.13 g of Oligomer dissolved in 40 ml acetonitrile was added while stirring the reaction mixture. Yield of total conjugated product was 77%.
d) Equal volume of the conjugated product from step (c) and water was taken. The pH of the solution was adjusted to 5.0 with glacial acetic acid then 0.4% (v/v) of phenol and 4% (v/v) of 0.3 N zinc chloride was added was added to the mixture and the pH was adjusted to 5.1 with 1 N NaOH. The mixture was kept over night at 4° C. for crystallization. Yield in this step was 90%,
e) the wet crystal pellet from step (d) was solubilized in 0.5M tris base solution to make a product concentration of 20 g/l. The pH of the solution was adjusted to 7.4 with 1 N NaOH. 0.02 mM trypsin and $13 \times 10^{-3}$ mM of carboxypeptidase B was added to the reaction mixture. At the end of 12 hrs product formed was IN-105 with a step yield of 85%,
f) A column packed with resin of particle size:10-15 μ, pore size: 120 Å was equilibrated using, 10% of buffer B, the reaction mixture from step (e) was diluted 1:10 with concentration of MeCN at 33% and pH adjusted to 3.5, washing was done with 15% B. Elution was done using step gradient. Yield of 58.6% were got, Buffer A:10 mM Sodium Acetate pH 7.0, Buffer B: 100% Acetonitrile.

g) the eluent from step (f) is further diluted and pH is adjusted to 7.5 before loading, and washing was done with 20% of buffer B. Elution was done using 22 to 32% of buffer B over 20 CVs. Fractions of 97% purity were got
[Buffer A:100 mM Tris pH 8.5; 20 mM Magnesium Chloride; Buffer B: Acetonitrile].

h) The elution pool from step (g) was taken and the concentration of IN-105 was brought down to 6 mg/ml by dilution with water. The pH of the sample is adjusted to 4.5 with glacial acetic acid. 0.6% (v/v) of phenol and 4% (v/v) of 0.3 N zinc chloride were added and pH was finally made to 5 and the mixture was kept at 4° C. overnight to form IN-105 crystals. The crystals were collected after centrifugation with a step yield of 90%.

Example 6

Exhaustive Conjugation a) SP-Sepharose column was equilibrated with buffer A (2 C.V), pH of the cell free broth was adjusted to 4.0 with glacial acetic acid and the supernatant was loaded on to column at 20 g/l load. Washing was done using Buffer A (1.5 C.V) and product was eluted at 0 to 100% B in 10 C.V. The elution pool was concentrated 8 times and Yield was 98%.
[Buffer A-10 mM Ammonium Acetate pH 4.0; Buffer B-1 M Ammonium Acetate pH 4.0].

b) the elution pool containing the IN-105 precursor was taken in 1:1 dilution with water and the pH was adjusted to 5.0 with 10 N NaOH. 0.4% (v/v) of phenol and 4% (v/v) of 0.3 N zinc chloride was added. The mixture kept under cold condition for 6-8 hrs for crystallization. The recovery of IN-105 precursor was 95%.

c) the wet crystal pellet was solubilized in DMSO to make the concentration of the product 60 g/ml. To the reaction mixture 0.001% (v/v) of triethyl amine was added. Oligomer was solubilized in tetrahydrofuran(THF) at a concentration of 0.4 M and added to the reaction mixture. At the end of 15 hrs exhaustively conjugated product with a yield of 80% was recovered.

d) equal volume of the conjugated product from step (c) and water was taken. The pH of the solution was adjusted to 5.0 with glacial acetic acid then 0.4% (v/v) of phenol and 4% (v/v) of 0.3 N zinc chloride was added was added to the mixture and the pH was adjusted to 5.1 with 1 N NaOH. The mixture was kept overnight at 4° C. for crystallization. Yield in this step was 90% e) the wet crystal pellet from step (d) was solubilized in 0.5 M tris base solution to make a product concentration of 25 g/l. The pH of the solution was raised to 7.4 with 1 N NaOH. 0.02 mM trypsin and $0.3 \times 10^{-3}$ carboxypeptidase was added to the reaction mixture. At the end of 14 hrs the IN-105 formed had a step yield 80% f) A column packed with resin of particle size:10-15 µ, pore size: 120 Å was equilibrated using 15% of buffer B; the reaction mixture from step (e) was diluted 1:10 and pH was adjusted to 7.0 before loading. Washing was done with 15% of buffer B and elution was done using 27 to 37% of buffer B over 20 Cvs. Fractions of 90% purity were got Buffer A: 100 mM Tris pH 8.0; 20 mM $MgCl_2$, pH 8.5. Buffer B:100% Acetonitrile.

g) The eluent from step (f) is further diluted and pH is adjusted to 9.0 before loading, and washing was done with 20% of buffer B. Elution was done using 20 to 35% of buffer B over 15 CVs. Fractions of 97% purity were got
[Buffer A:100 mM Tris pH 9.0; 20 mM Magnesium Chloride; Buffer B: Acetonitrile].

h) The elution pool from step (g) was taken and the concentration of IN-105 was brought down to 6 mg/ml by dilution with water. The pH of the sample is adjusted from 8.3 to 4.5 with glacial acetic acid. 0.6% (v/v) of phenol and 4% (v/v) of 0.3 N zinc chloride were added and pH was finally made to 5 and the mixture was kept at 4° C. overnight to form crystals. The crystals were collected after centrifugation with a step yield of 90%.

Example 7

Exhaustive Conjugation a) SP-Sepharose column was equilibrated with buffer A (2 C.V), pH of the cell free broth was adjusted to 4.0 with glacial acetic acid and the supernatant was loaded on to column at 45 g/l load. Washing was done using Buffer A (1.5 C.V) and product was eluted at 60% B. The elution pool was concentrated 8 times and Yield was 95%,
[Buffer A-10 mM Ammonium Acetate pH 4.0; Buffer B-1 M Ammonium Acetate pH 4.0]

b) the of elution pool containing the IN-105 precursor was taken in 1:1 dilution with water and the pH was adjusted to 5.0 with 10 N NaOH. 0.4% (v/v) of phenol and 4% (v/v) of 0.3 N zinc chloride was added. The mixture kept under cold condition for 6-8hrs for crystallization. The recovery of IN-105 precursor was 95%, c) the wet crystal pellet was solubilized in DMSO to make the concentration of the product 60 g/ml. To the reaction mixture 0.001% (v/v) of triethyl amine was added. Oligomer was solubilized in tetrahydrofuran(THF) at a concentration of 0.4 M and added to the reaction mixture. At the end of 15 hrs exhaustively conjugated product with a yield of 80% was recovered.

d) Equal volume of the conjugated product from step (c) and water was taken. The pH of the solution was adjusted to 5.0 with glacial acetic acid then 0.4% (v/v) of phenol and 4% (v/v) of 0.3 N zinc chloride was added was added to the mixture and the pH was adjusted to 5.1 with 1 N NaOH. The mixture was kept over night at 4° C. for crystallization. Yield in this step was 90%, e) the wet crystal pellet from step (d) was solubilized in 0.5 M Tris base solution to make a product concentration of 25 g/l. The pH of the solution was raised to 7.4 with 1 N NaOH, to the reaction mixture 0.02 mM trypsin and $0.3 \times 10^{-3}$ carboxypeptidase B were added. At the end of 14 hrs the IN-105 formed had a step yield 80% f) A column packed with resin of particle size:10-15 µ, pore size: 120 Å was equilibrated using 10% of buffer B, the reaction mixture from step (e) was diluted 1:10 with concentration of MeCN at 15% and pH adjusted to 3.5 and load filtered through 5 micron filter; washing was done with 15% B. Elution was done using 17 to 23% of buffer B over 20 Cvs. 94.2% pure protein with a yield of 77% were got.
[Buffer A: 250 mM Acetic Acid, Buffer B: Acetonitrile]

g) the eluent from step (f) is further diluted and pH is adjusted to 9.0 before loading, and washing was done with 20% of buffer B. Elution was done using 22 to 32% B over 15 CVs. Fractions of 97% purity were got
[Buffer A:100 mM Tris pH 9.0; 20 mM Magnesium Chloride; Buffer B: Acetonitrile]

h) The elution pool from step (g) was taken and the concentration of IN-105 was brought down to 6 mg/ml by dilution with water. The pH of the sample is adjusted from 8.3 to 4.5 with glacial acetic acid. 0.6% (v/v) of phenol and 4% (v/v) of 0.3 N zinc chloride were added and pH was finally made to 5 and the mixture was kept at 4° C. overnight to form IN-105 crystals. The crystals were collected after centrifugation with a step yield of 90%.

We claim:

1. A process for the preparation of an insulin conjugate IN-105 comprising
   i) cloning and expressing the synthetic polypeptide precursor G-A-V-R-[B-Chain]-R-D-A-D-D-R-[A-Chain] represented by the formula IP-F (SEQ ID NO: 11), in yeast;
   ii) fermenting the yeast clone expressing IP-F;
   iii) isolating and purifying of the IP-F;
   iv) conjugating of the IP-F with an oligomer, wherein the oligomer is conjugated at the B29 position of the IP-F and at the Gly 1 of the leader chain G-A-V-R
   v) treating the IP-F oligomer with a protease; and
   vi) purifying the active insulin-oligomer conjugate.

2. A process of claim 1 i), wherein the yeast is a methylotropic yeast.

3. A process of claim 2, wherein the methylotropic yeast is *Pichia*.

4. A process of claim 1, wherein the precursor IP-F is isolated from the broth by ion exchange chromatography followed by crystallization.

5. A process of claim 4, wherein the crystallization is carried out in phenol and $ZnCl_2$.

6. A process of claim 4, wherein the precursor IP-F is treated with activated oligomer.

7. A process of claim 6, wherein the activated oligomer is succinamide derivative of $C_{14}H_{23}NO_8$.

8. A process of claim 1, wherein the conjugation of IP-F with an activated oligomer is carried out in one or more solvents selected from borate buffer, acetonitrile, and DMSO.

9. A process of claim 1, wherein the oligomer is conjugated at Lys-$B^{29}$ of the B chain in IP-F.

10. A process of claim 1, wherein the IP-F-oligomer conjugate is IP-F-OC—$CH_2$—$CH_2$—$(OCH_2CH_2)_3$—$OCH_3$.

11. A process of claim 1, wherein the IP-F-oligomer conjugate is further subjected to crystalization.

12. A process of claim 1, wherein the IP-F-oligomer conjugate is treated with a protease to get an active insulin-oligomer conjugate.

13. A process of claim 12, wherein the protease is selected from trypsin or carboxypeptidase B or mixture thereof.

14. A process of claim 12, wherein the active insulin-oligomer conjugate is purified by RP-HPLC and crystallization.

15. A process of claim 14, wherein the active insulin-oligomer conjugate is insulin-OC—$CH_2$—$CH_2$—$(OCH_2CH_2)_3$—$OCH_3$.

* * * * *